(12) United States Patent
Böttger et al.

(10) Patent No.: US 8,763,350 B2
(45) Date of Patent: *Jul. 1, 2014

(54) METHOD FOR FILLING DUAL-CHAMBER SYSTEMS IN PRE-STERILIZABLE CARRIER SYSTEMS

(75) Inventors: Frank Böttger, Ravensburg (DE); Benjamin Böbst, Mittelbiberach (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 491 days.

This patent is subject to a terminal disclaimer.

(21) Appl. No.: 12/999,039

(22) PCT Filed: Jun. 16, 2009

(86) PCT No.: PCT/EP2009/004313
§ 371 (c)(1),
(2), (4) Date: Dec. 14, 2010

(87) PCT Pub. No.: WO2009/153018
PCT Pub. Date: Dec. 23, 2009

(65) Prior Publication Data
US 2011/0094189 A1    Apr. 28, 2011

(30) Foreign Application Priority Data
Jun. 19, 2008   (DE) .......................... 10 2008 030 268

(51) Int. Cl.
*B65B 3/00* (2006.01)
*B65B 7/28* (2006.01)
*A61J 1/20* (2006.01)

(52) U.S. Cl.
CPC ............... *B65B 3/003* (2013.01); *B65B 7/2821* (2013.01); *A61J 1/2093* (2013.01)
USPC .................... 53/440; 53/468; 53/471; 53/489

(58) Field of Classification Search
CPC ..... A65B 7/2821; A65B 3/003; A61J 1/2093; A61M 5/284; A61M 5/19
USPC .................................. 53/440, 468, 471, 489
See application file for complete search history.

(56) References Cited

U.S. PATENT DOCUMENTS 3,696,579 A * 10/1972 Narusawa et al. ............... 53/440
3,807,119 A *  4/1974 Shields .......................... 53/471
(Continued)

FOREIGN PATENT DOCUMENTS

DE    10028823       12/2001
DE    10341978 A1     9/2004
(Continued)

OTHER PUBLICATIONS

International Search Report and Written Opinion of the ISA, ISA/EP, mailed Oct. 1, 2009, for PCT/EP2009/004313, 6 pages.

(Continued)

*Primary Examiner* — Stephen F Gerrity
(74) *Attorney, Agent, or Firm* — Harness, Dickey & Pierce, P.L.C.

(57) ABSTRACT

A method for filling dual-chamber systems (3) in pre-sterilizable carrier systems (1) is proposed, which comprises the following steps: provision of at least one washed, siliconized and sterilized dual-chamber system (3) with respectively one separating element separating the two chambers (5, 5') from one another in a magazine (9), which accommodates the at least one dual-chamber system (3), wherein the magazine (9) is arranged in a container (11) sealed with a closure element (13); feeding the container (11) into a clean room; opening the container (11) and filling a first chamber (5) of the at least one dual-chamber system (3); closing the first chamber (5) with a gas-permeable closure element (19); freeze drying the solution (L1) contained in the first chamber (5); closing the first chamber (5) with a closure element (19); filling a second chamber (5') of the at least one dual-chamber system (3); closing the second chamber (5'); discharge from the clean room.

12 Claims, 5 Drawing Sheets

(56) References Cited

U.S. PATENT DOCUMENTS

| | | | |
|---|---|---|---|
| 4,716,710 A * | 1/1988 | Galy et al. | 53/440 |
| 4,729,208 A * | 3/1988 | Galy et al. | 53/440 |
| 5,080,649 A | 1/1992 | Vetter | |
| 5,184,450 A * | 2/1993 | Galy et al. | 53/440 |
| 5,185,985 A * | 2/1993 | Vetter et al. | 53/299 |
| 5,435,076 A * | 7/1995 | Hjertman et al. | 34/296 |
| 5,439,703 A | 8/1995 | Kanda et al. | |
| 5,788,670 A * | 8/1998 | Reinhard et al. | 604/89 |
| 5,884,457 A * | 3/1999 | Ortiz et al. | 53/468 |
| 6,189,292 B1 | 2/2001 | Odell et al. | |
| 6,224,568 B1 | 5/2001 | Morimoto et al. | |
| 6,263,641 B1 | 7/2001 | Odell et al. | |
| 6,807,797 B2 * | 10/2004 | Forsberg et al. | 53/440 |
| 6,817,987 B2 * | 11/2004 | Vetter et al. | 604/85 |
| 2001/0042317 A1 * | 11/2001 | Yarborough et al. | 34/287 |
| 2003/0100866 A1 * | 5/2003 | Reynolds | 604/187 |
| 2004/0138611 A1 * | 7/2004 | Griffiths et al. | 604/82 |
| 2005/0113763 A1 * | 5/2005 | Reynolds | 604/187 |
| 2005/0177100 A1 | 8/2005 | Harper et al. | |
| 2005/0193586 A1 * | 9/2005 | Yarborough et al. | 34/285 |
| 2006/0048844 A1 * | 3/2006 | Merrill et al. | 141/85 |
| 2006/0054523 A1 | 3/2006 | Porret et al. | |
| 2006/0178644 A1 * | 8/2006 | Reynolds | 604/232 |
| 2007/0060875 A1 | 3/2007 | Bassarab et al. | |
| 2007/0060876 A1 * | 3/2007 | Bassarab et al. | 604/88 |
| 2007/0129673 A1 * | 6/2007 | Bassarab et al. | 604/85 |
| 2007/0186510 A1 * | 8/2007 | Wittland et al. | 53/471 |
| 2008/0275387 A1 * | 11/2008 | Yeadon et al. | 604/82 |
| 2009/0018496 A1 | 1/2009 | Harper et al. | |
| 2009/0283493 A1 | 11/2009 | Witowski | |
| 2011/0094188 A1 * | 4/2011 | Bottger et al. | 53/425 |

FOREIGN PATENT DOCUMENTS

| | | |
|---|---|---|
| DE | 102005038458 A1 | 2/2007 |
| EP | 0440846 A | 8/1991 |
| EP | 0879611 A2 | 11/1998 |
| EP | 0882441 A2 | 12/1998 |
| JP | 10314305 | 12/1998 |
| JP | 2002505921 A | 2/2002 |
| JP | 2004513708 A | 5/2004 |
| JP | 2005521478 A | 7/2005 |
| WO | 9945985 A1 | 9/1999 |
| WO | 03082369 A2 | 10/2003 |
| WO | 2005/039669 A2 | 5/2005 |
| WO | 2006053550 A1 | 5/2006 |
| WO | 2009/153018 | 12/2009 |

OTHER PUBLICATIONS

International Search Report for PCT/EP2009/004308, ISA/EP, Rijswijk, NL, mailed Sep. 15, 2009, 3 pages.

English Translation of International Preliminary Report on Patentability for PCT/EP2009/004313, incorporating the English Translation of the Written Opinion of the ISA, 5 pages.

English Translation of International Preliminary Report on Patentability for PCT/EP2009/004308, incorporating the English Translation of the Written Opinion of the ISA, 5 pages.

First Office Action regarding Japan Patent Application No. 2011-513941, mailed Feb. 26, 2013. Translation provided by Suzuye & Suzuye, 5 pages.

Office Action regarding Russia Patent Application No. 2011101704/13, dated Feb. 12, 2013, 3 pages.

* cited by examiner

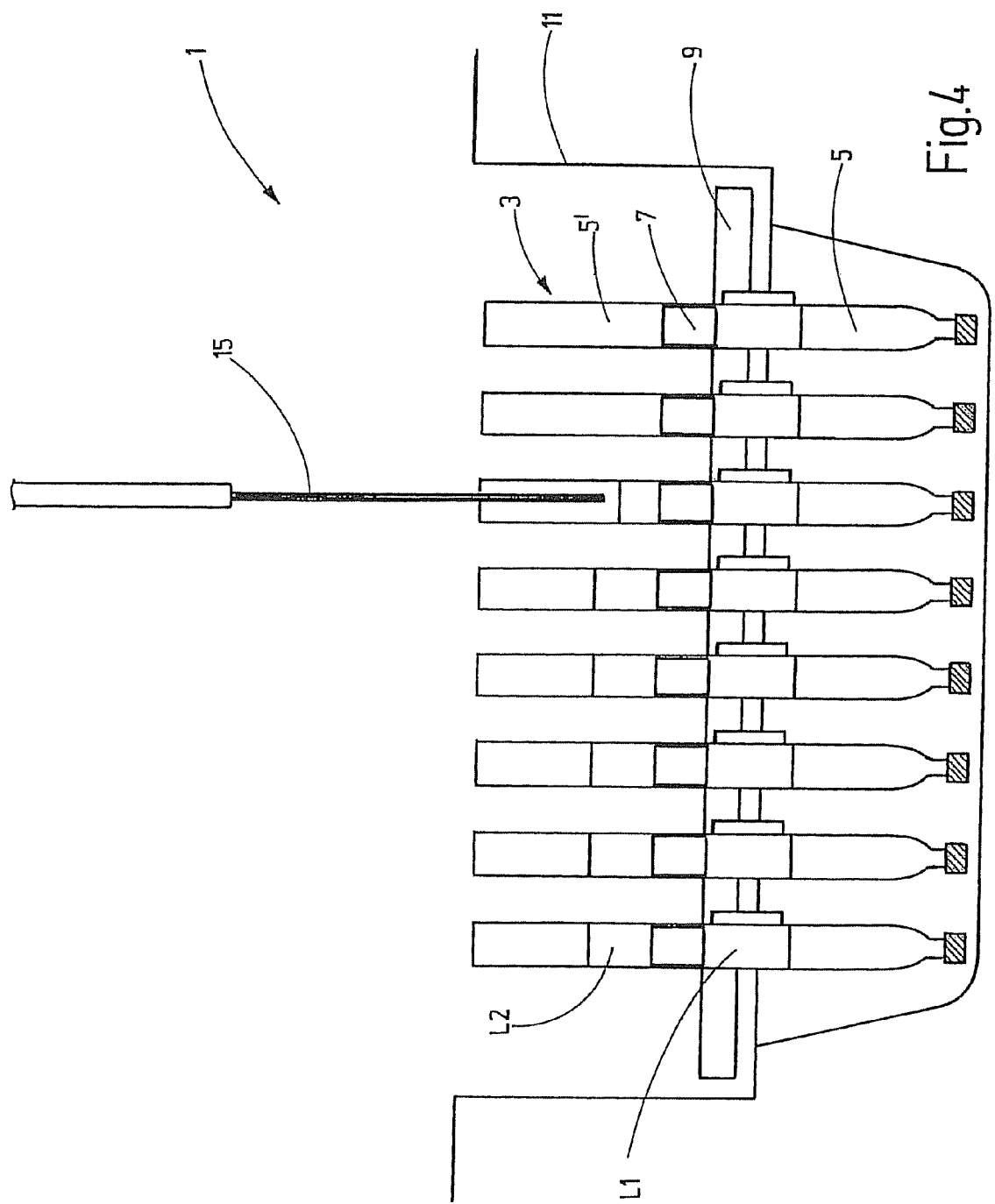

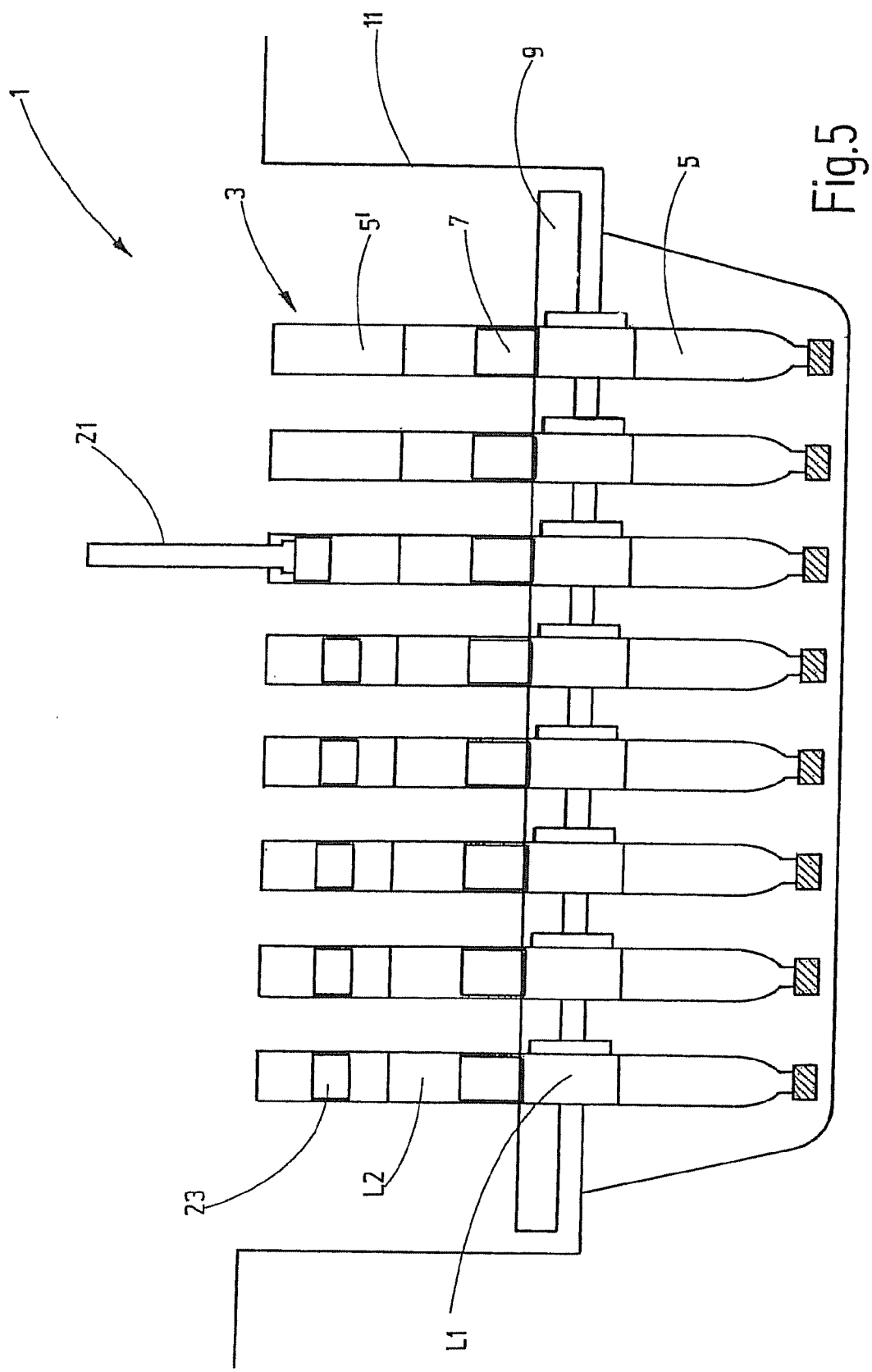

METHOD FOR FILLING DUAL-CHAMBER SYSTEMS IN PRE-STERILIZABLE CARRIER SYSTEMS

CROSS-REFERENCE TO RELATED APPLICATIONS

This application is a 371 U.S. National Stage of International Application No. PCT/EP2009/004313, filed Jun. 16, 2009. This application claims priority to German Patent Application No. 10 2008 030 268.6, filed Jun. 19, 2008. The disclosures of the above applications are entirely incorporated by reference herein.

FIELD

The invention relates to a method for filling dual-chamber systems in pre-sterilizable carrier systems as well as a pre-sterilizable carrier system.

BACKGROUND

Pre-sterilizable carrier systems and methods for the filling thereof are known. A known carrier system comprises usually washed, siliconized and sterilized syringes, which are placed in a magazine after the washing and siliconizing step. The magazine—also referred to as a nest—is subsequently placed in a container which is then sealed with a closure element, preferably a gas-permeable membrane film, and sterilized via suitable sterilization methods. An ethylene oxide gassing is often used hereby. Because the closure element is gas-permeable, the sterilization gas can penetrate into the interior of the container and also sterilize the contents of the container, that is, the washed and siliconized syringes as well as the magazine holding them. The container does not need to be opened again after the sterilization step and can be delivered in the present form directly to a customer or to a filling line. The gas-permeable closure element namely has a filter effect such that although it is permeable for a sterilization gas, it closes the container in a tight and sterile manner with respect to germs, viruses and bacteria. As long as the container remains closed, the sterility of the contents thereof is therefore ensured. With a customer who typically operates a filling machine for filling the syringes or other hollow bodies with pharmaceutical contents held by the container, the container is opened, the hollow bodies are filled and closed, whereupon the container can be again closed and transported to the end customer. Of course, the filled and closed hollow bodies can also be removed from the container and passed to the end customer in different packaging units. The essential factor in the cited pre-sterilized carrier systems and the method for the filling thereof is that a standardized packaging form is used which can be used in connection with standardized filling lines. The hollow bodies to be filled therefore do not need to be removed from the container before filling, whereby a complex process step is omitted. Furthermore, it is advantageous that the hollow bodies can be sterilized jointly in an already packaged form, after which shipping or further processing can take place without complex interim steps such as a new packaging in a pre-sterilized further packaging unit or repackaging being necessary. In a manufacturing pharmaceutical company that carries out the filling, a clean room or process step for preparing the hollow bodies can be omitted, since they are supplied ready for filling.

The production and/or preparation of the hollow bodies can also be carried out as an in-line process with the filling, if a hot-air tunnel is provided between the sterilization device and the clean room in which the filling takes place.

The known pre-sterilizable carrier systems and the methods for the filling thereof, however, are designed only for single-chamber systems, that is, single-chamber syringes, single-chamber carpules or vials. In order to fill dual-chamber systems such as dual-chamber syringes or carpules, more complex methods and carrier devices are therefore still necessary.

If dual-chamber systems are used in conventional filling methods in connection with a freeze drying step for a solution located in one of the two chambers, special closure elements—so-called Lyo closures—are used. A closure element of this type is thereby assigned to each individual dual-chamber system. These Lyo closures have two click-stop positions on the dual-chamber system: in a first click-stop position they seal the dual-chamber system in a manner such that a gas exchange between the interior of the chamber closed with the closure element and the environment can take place. In a second click-stop position the closure element closes the chamber completely. In conventional processes the dual-chamber systems are sorted in heavy, reusable metal magazines. These have the disadvantage of being difficult to handle due to their great weight. Furthermore, they have to be laboriously cleaned and sterilized, typically autoclaved, before each use.

SUMMARY

The object of the invention is therefore to create a method for filling at least one dual-chamber system in connection with a freeze-drying step using at least one closure element embodied as a Lyo closure in at least one pre-sterilizable carrier system.

This is also characterized by the following steps: at least one washed, siliconized and sterilized dual-chamber system with respectively one separating element separating the two chambers from one another in a magazine, which accommodates the at least one dual-chamber system, preferably a number of systems of this type, is provided, wherein the magazine is arranged in a container sealed with a closure element. The sealed container is fed into a clean room. It is opened there and a first chamber of the at least one dual-chamber system is filled. This first chamber is closed with a gas-permeable closure element and the material contained in the first chamber is freeze dried. The first chamber is closed with a closure element. A second chamber of the at least one dual-chamber system is filled. The second chamber is also closed and the at least one filled dual-chamber system is discharged from the clean room. Through the use of standardized pre-sterilizable carrier systems, a manufacturing pharmaceutical company is relieved of the complex preparation of the hollow bodies, and the use of standardized filling lines is possible.

This comprises the following steps: at least one washed, siliconized and sterilized dual-chamber system is provided, which has a separating element separating the two chambers from one another. A magazine accommodates the at least one dual-chamber system, wherein the magazine is arranged in a container that is sealed with a closure element. The container is fed into a clean room. It is opened and the first chamber of the at least one dual-chamber system is filled. The first chamber is closed with a gas-permeable closure element. The container is closed with a gas-permeable closure element. This is followed by a process step in which the material contained in the first chamber of the at least one dual-chamber system is freeze dried. The solvent vapor hereby sublimates through the gas-permeable closure elements of the first chamber of the at least one dual-chamber system and the gas-permeable closure element of the container. After the freeze drying the first chamber is closed with a closure element. The container is opened and a second chamber of the at least one dual-chamber system is filled and closed. The at least one dual-chamber system is discharged from the clean room.

A method is also preferred which is characterized in that the magazine that accommodates the at least one dual-chamber system comprises plastic, preferably is composed of plastic. The magazine is hereby very light and therefore also easy to handle. It can furthermore be determined as a product for a single use, so that it can be disposed of after use. Thus the heavy metal magazines that are usual in the known carrier systems are omitted which on the one hand are difficult to handle and on the other hand have to be autoclaved in order to keep them sterile. With the carrier system according to the invention, however, a new plastic magazine is also supplied with each new delivery, which magazine is assigned to precisely one dual-chamber system or in particular to a batch of dual-chamber systems and is disposed of after use. In addition to the discontinuation of complex process steps, this leads in particular to making a handling of dual chamber systems possible that is easily reproducible with respect to the sterility thereof.

A method is also preferred in which the container comprises plastic, preferably is composed of plastic. It is also preferably provided here that the container is used once and is disposed of after use. A container is uniquely assigned to each batch of dual-chamber systems, so that here too the sterility of the batches is ensured with very good reproducibility.

A method is also preferred in which in particular the plastic that the container comprises or of which the container is composed is elastically deformable. In conventional methods the Lyo closures are closed after the freeze during in that the vertical spacing of the shelf racks of the device for freeze drying is reduced in a manner such that the Lyo closures are pushed from their first click-stop position into their second click-stop position. This is possible since the known carrier systems of metal hold the dual-chamber systems only at the side and do not have a height that is greater than the vertical extension of the dual-chamber systems. In contrast thereto, the container of a pre-sterilizable carrier system is embodied such that the walls thereof have a greater height than the dual-chamber systems so that they are completely and safely embedded in the container. This means that with a rigid container the Lyo closures have to be pushed into their second click-stop position by a device that can engage into the container. However, if the container is made of an elastically deformable plastic, the known closure method for the Lyo closures can be used. Namely, if the shelf racks of the freeze dryer move towards one another such that their vertical spacing is reduced, they compress the elastically deformable container along its vertical extension so that the Lyo closures can be forced into their second click-stop position. A pre-sterilizable carrier system that has a container of an elastically deformable plastic thus makes it possible to shift the Lyo closures of the dual-chamber systems in a very simple and known manner into a position in which they tightly seal the first chamber of the dual-chamber system.

A method is also preferred in which, after the filling of the first chamber of the at least one dual chamber system and the closure of the first chamber and of the container with a gas-permeable closure element, the container first is discharged from the clean room and is placed into a device for freeze drying arranged outside the clean room. The freeze drying takes place there at the end of which the container is removed from the device and in turn is fed into a clean room. If the method is expanded by this step, it is possible to separate the aseptic filling of the pharmaceutical content from the freeze drying completely, wherein this does not need to take place under aseptic conditions. This is possible because the container is provided with a gas-permeable closure element which, although it allows the sublimated solvent vapor during the freeze drying process to pass from the interior of the container to the outside, prevents germs, viruses and bacteria from penetrating into the container. The interior of the container thus remains aseptic even when the environment in the freeze dryer is not kept sterile. In this manner complex cleaning and disinfecting steps for the freeze dryer can be omitted, and the freeze dryer does not need to be arranged inside the clean room, either.

In this context a method is also preferred that is characterized in that the device for freeze drying itself is not sterile and/or aseptic. As has been said, this is possible due to the closing of the container with a gas-permeable closure element which, however, is not permeable for viruses, bacteria and germs.

Further advantageous embodiments regarding the claimed method are shown by the subordinate claims.

Moreover, it is the object of the invention to provide a pre-sterilizable carrier system for at least one dual-chamber system.

This object is attained through a pre-sterilizable carrier system comprising at least one washed, siliconized and sterilized dual-chamber system, which has a separating element that separates the two chambers from one another. Furthermore, the pre-sterilizable carrier system has a magazine that serves to accommodate the at least one dual-chamber system. It also comprises a container. The magazine that accommodates the at least one dual-chamber system can be arranged in the container, wherein this can be sealed with a closure element. A closed container is thus produced, in which a magazine is arranged, which comprises at least one washed, siliconized and sterilized dual-chamber system. It is particularly preferred when the entire container is sterilized in the interior. Through the sealing, such pre-sterilizable carrier systems equipped with at least one dual-chamber system can be produced ahead and stored, wherein the content remains sterile.

A pre-sterilizable carrier system is also preferred in which the magazine comprises plastic, preferably is composed of plastic. In this case the magazine is particularly light and moreover can be disposed of after the use of the pre-sterilizable carrier system, so that complex cleaning or autoclaving steps are omitted. Moreover, each batch of dual-chamber systems is assigned to precisely one magazine so that a handling that can be easily reproduced with respect to the sterility is possible.

A pre-sterilizable carrier system is also preferred which is characterized in that the container comprises plastic, preferably is composed of plastic. Also in this case the container is provided for a single use, so that each batch of dual-chamber systems is assigned precisely to one container. This also increases the reproducibility of the handling with respect to its sterility.

A pre-sterilizable carrier system is preferred in which in particular the plastic that the container comprises or of which the container is preferably composed is elastically deformable. It is hereby possible to push Lyo closures that are located in a first click-stop position on the dual-chamber systems after freeze drying by reducing the vertical spacing between the shelf racks of the device for freeze drying into a second click-stop position in which they tightly close the first chamber of the dual-chamber systems. The container, the walls of which have a greater height than the dual chamber systems so that they completely surround them, is thereby compressed along its vertical extension. It is thus possible to push the Lyo closures in a very simple and known manner into a second click-stop position in which they tightly close the first chamber of the dual-chamber system.

Furthermore, a pre-sterilizable carrier system is preferred in which the closure element for the container is gas-permeable. In this case the container already equipped with the magazine and the dual-chamber systems by the manufacturer can be closed and subsequently sterilized in that the gas determined for sterilization penetrates through the gas-permeable closure element into the interior of the container. After the sterilization it is no longer necessary to open the container and it can be further transported immediately, for example, to a filling line. Because the container is already finally closed during the sterilization, germ-containing material cannot penetrate from outside into the interior of the container through a subsequent opening or closing. The word gas-permeable thereby indicates that, although the closure element allows gases and vapors to pass through, it prevents germs, viruses or bacteria from penetrating into the interior of the container.

BRIEF DESCRIPTION OF THE DRAWINGS

The invention is explained in more detail below based on the drawings in which:

FIG. 4 is a diagrammatic representation of the filling of a second chamber of the dual-chamber systems in the method; and FIG. 5 is the closure of the second chamber of the dual-chamber systems in the method.

DETAILED DESCRIPTION

Figure 1:
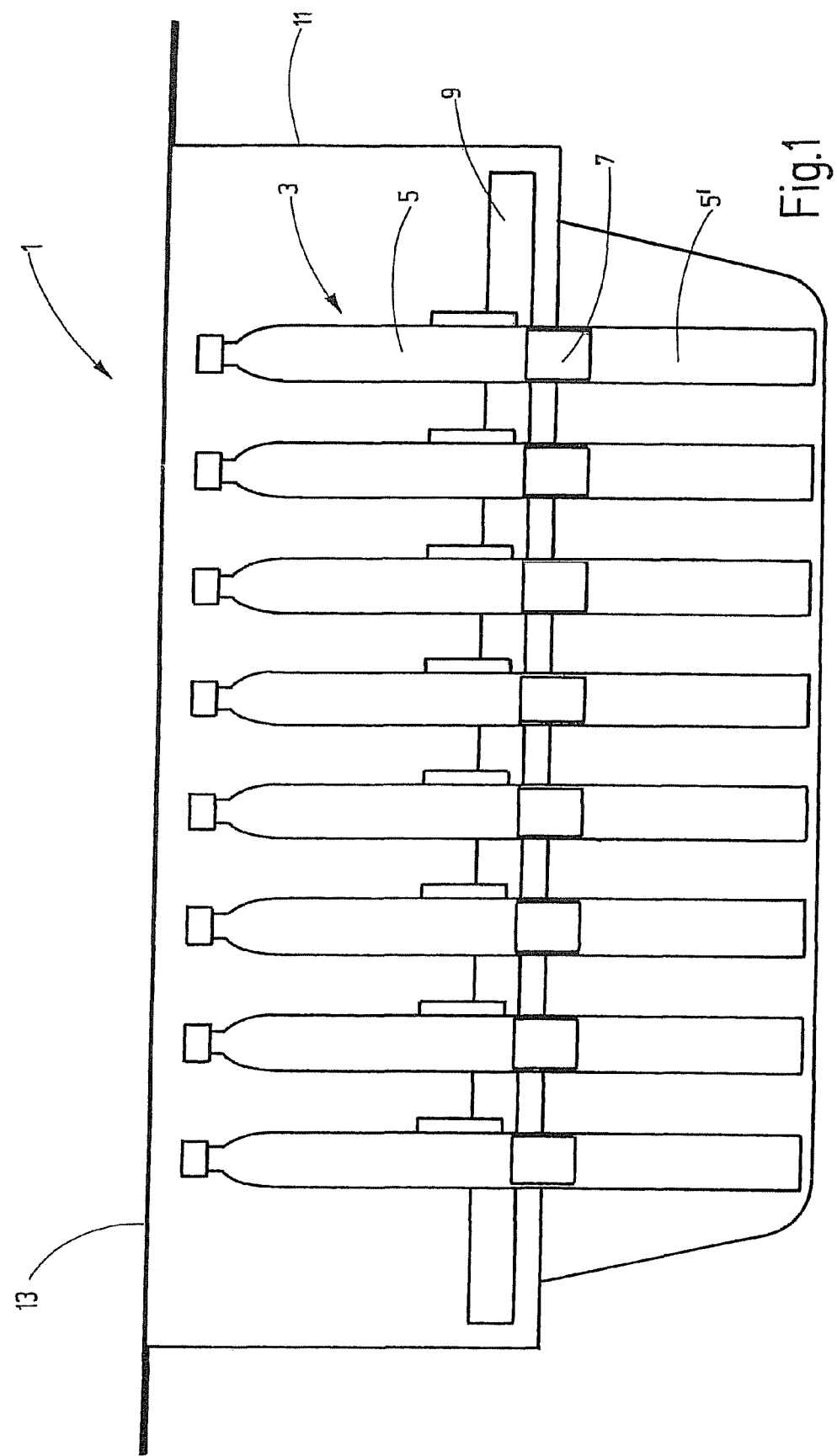
FIG. 1 is a diagrammatic view of a pre-sterilizable carrier system in accordance with the present teachings.

FIG. 1 shows diagrammatically an exemplary embodiment of a pre-sterilizable carrier system 1. It comprises at least one washed, siliconized and sterilized dual-chamber system 3 with two chambers 5, 5', which are separated from one another by a separating element 7. The dual-chamber systems 3 are accommodated by a magazine 9, which in turn can be arranged in a container 11. This is sealed by a closure element 13.

The container 11 can comprise plastic, preferably it is composed of plastic. The magazine 9 can also comprise plastic and is preferably composed of plastic. Both elements can be determined for a single use in this manner, so that each batch of dual-chamber systems 3 is respectively assigned to a magazine 9 and a container 11. The cleaning and autoclaving steps necessary in the known methods hereby are omitted which are provided for sterilization of the reusable metal magazines. Moreover, both elements composed of plastic are easy to handle, in particular lighter than the known heavy carrier systems of metal.

The closure element 13 for the container 11 is preferably embodied in a gas-permeable manner so that the completely equipped and sealed container 11 can be sterilized in the closed state in that it is introduced into an atmosphere that comprises a gas determined for sterilization or a vapor determined for sterilization. The gas or the vapor can penetrate through the closure element 13 into the interior of the container 11 and thus in particular also sterilize the interior of the container 11 as well as the dual-chamber systems 3 contained therein and the magazine 9.

The different methods are now explained in more detail based on FIGS. 2 through 5.

Firstly the pre-sterilizable carrier system 1 is provided and fed into a clean room. Then the closure element 13 is removed, so that the dual-chamber systems 3 are accessible.

Figure 2:
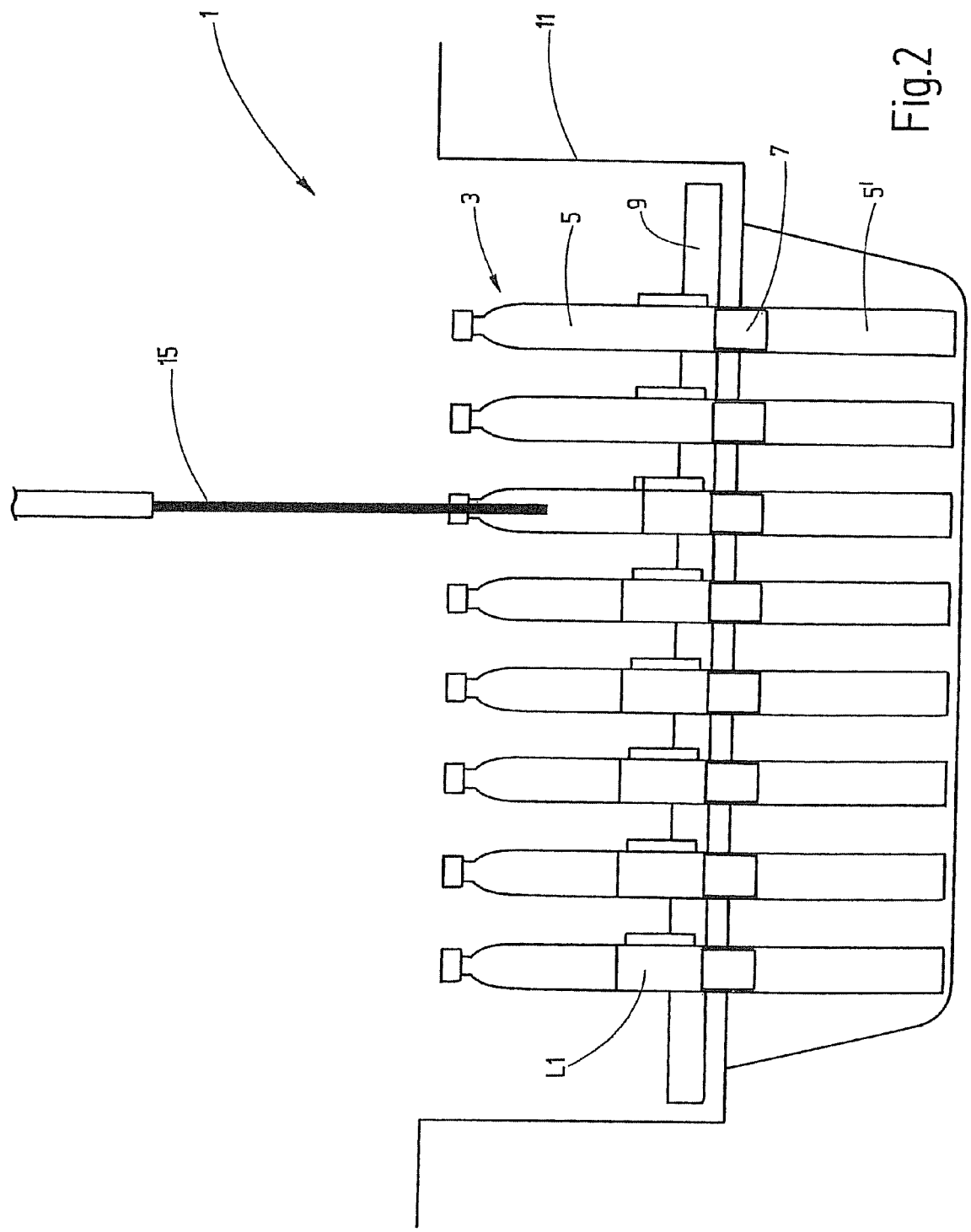
FIG. 2 is a diagrammatic representation of the step of filling a first chamber of the dual-chamber systems in a method according to the invention.

FIG. 2 shows the step of filling a first chamber 5 of the dual-chamber systems 3. Identical elements and elements with the same function are provided with the same reference numbers so that in this respect we refer to the description above. A delivery device 15 is provided through which a first solution L1 of an active substance or an auxiliary substance can be introduced into a first chamber 5 of the dual-chamber systems 3.

Figure 3:
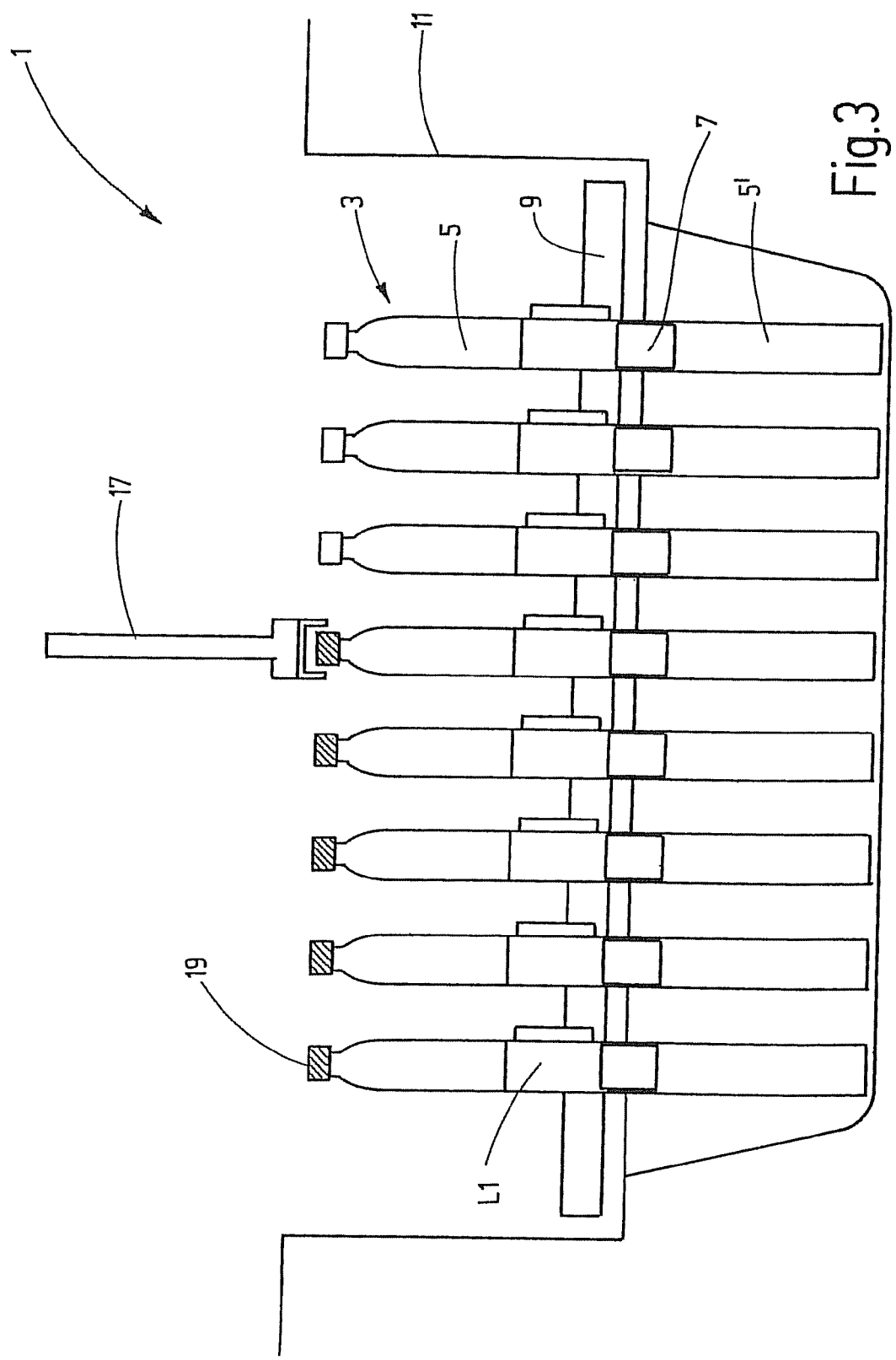
FIG. 3 is a diagrammatic view of the closure of the first chamber of the dual-chamber systems with a gas-permeable closure element in the method.

After the filling of the first chamber 5 of the dual-chamber systems 3, the first chamber can be closed, as shown in FIG. 3. Identical elements and elements with the same function are provided with identical reference numbers so that in this respect we refer to the description above. A first closure device 17 is provided, with which the first chamber 5 of the dual-chamber systems 3 can be closed in a gas-permeable manner with respectively one closure 19. The closure 19 is embodied as a Lyo closure and is brought by the first closure device 17 into a first click-stop position so that the first chamber 5 of the dual-chamber systems is closed in a gas-permeable manner.

The container 11 can now be placed into a device for freeze drying. Since the container is open, the device for freeze drying must likewise be located in a clean room. It is possible to feed the open container 11 through a hot-air tunnel from the first clean room into a second clean room in which the device for freeze drying is located. However, this can also be located in the first clean room so that no hot-air tunnel needs to be provided. During the freeze drying, the solvent contained in the first chamber 5 sublimates through the gas-permeable closure 19 of the first chamber. After the freeze drying step has been concluded, the closures 19 are shifted from their first click-stop position into a second click-stop position in which they tightly close the first chamber 11 of the dual-chamber systems 3. This preferably still takes place inside the device for freeze drying, in that the shelf racks thereof are moved towards one another in the vertical direction such that their spacing is reduced and the closures 19 are hereby forced into their second click-stop position. It can be provided to this end that the plastic that the container comprises and of which it is preferably composed is elastically deformable so that it can be compressed in the vertical direction. Of course, the container 11 can also first be removed from the device for freeze drying, whereupon in a second step the closures 19 are then pushed into their second click-stop position by any desired device that optionally compresses the walls of the container 11 or engages into the interior of the container 11.

The container 11 can also be closed by a gas-permeable closure element 13, preferably a gas-permeable membrane film, before the freeze drying step. The container 11 sealed in this manner can be placed into a device for freeze drying where the solvent contained in the first chamber 5 sublimates through the gas-permeable closure 19 of the first chamber and the gas-permeable closure element 13 of the container so that ultimately the active substance and/or auxiliary substance present in the dual-chamber systems 3 is freeze dried. Since the container 11 is hygienically sealed by the gas-permeable closure element 13, it is possible to provide the device for freeze drying outside the clean room. The container 11 can thus be discharged from the clean room and placed into an external freeze drying device. This device does not need to be kept sterile and/or aseptic itself, since no germs, viruses or bacteria can penetrate through the closure element 13 into the interior of the container 11. Thus in particular the dual-chamber systems 3 remain sterile or aseptic, even if the freeze drying is carried out in a non-sterile and/or aseptic environment.

After the freeze drying, the closures 19 are pushed from their first click-stop position into a second click-stop position in which they close the first chamber 5 of the dual chamber systems 3 in a sealing manner. This preferably still takes place inside the device for freeze drying. For this purpose it is provided that the container 11 comprises an elastically deformable plastic, preferably is composed thereof. By a reduction of the vertical spacing of the shelf racks of the device for freeze drying, the container 11 can thus be compressed in the direction of its vertical extension. The closures 19 can hereby be pushed from a first click-stop position into a second click-stop position in which they tightly surround the dual-chamber systems 3. During this process, the gas-permeable closure element 13 is not released from the container 11, so that this remains closed in a germ-free manner. Of course, it is also possible to first remove the container 11 from the device for freeze drying and in a second step to push the closures 19 in a suitable manner into their second click-stop position. This can take place either still outside the clean room or after feeding into the first or into a further clean room.

After the closures 19 have been pushed into their second click-stop position, they can be closed with a tamper-proof closure. The closures 19 thereby remain on the dual-chamber systems 3, and the tamper-proof closure is placed onto the closures 19. With a use of the dual-chamber systems 3, the tamper-proof closure serves to indicate whether the closures 19 have been opened again after the final closure in the production line or whether the tamper-proof closure is maintained. In this respect the tamper-proof closures are guarantee closures that signalize to a user the undamaged seal of the first chamber 5 of the dual-chamber systems 3 and in the same manner also indicate that the contents of the chamber 5 have not been contaminated or changed.

During the freeze drying, the dual-chamber systems 3 are embedded into the container 11 and securely protected from thermal stray radiation or other interfering factors.

After the freeze drying and the closure of the first chamber 5, the container 11, where applicable, needs to be opened again so that the dual-chamber systems 3 are accessible. A second chamber 5' is filled. This is possible in a particularly simple manner when the magazine 9 is turned over. In this case it is provided that the magazine 9 holds the dual-chamber systems 3 such that they are held securely therein regardless of the orientation of the magazine 9. It is thus ensured that the dual-chamber systems 3 do not slip out of the magazine, even when the magazine 9 is turned over. After the magazine 9 has been turned over, the magazine is preferably inserted into the container 11 again, wherein a second chamber 5' of the dual chamber systems 3 is now accessible through the opening of the container 11.

FIG. 4 shows diagrammatically the filling of the second chamber 5' of the dual-chamber systems 3. Identical elements and elements with the same function are provided with the same reference numbers so that in this respect we refer to the description above. Here too a delivery device 15 is provided through which a second medium L2 can be introduced into the second chamber 5' of the dual-chamber systems 3. The second medium L2 can be the solution of a further active substance and/or auxiliary substance, but it can also be a—preferably pure—solvent or a solvent mixture.

After the filling of the second chamber 5' of the dual-chamber systems 3, this can also be closed.

FIG. 5 shows diagrammatically the step of closing the second chamber 5' of the dual chamber systems 3. Identical elements and elements with the same function are provided with the same reference numbers, so that in this respect we refer to the description above. The second chamber 5' is closed with the aid of second closure device 21 with a closure element that is embodied here by way of example as a plug 23. This can preferably be displaced in the dual chamber system 3 so that compressive forces can be introduced via the plug into the second chamber 5' and ultimately into the separating element 7, which lead to an activation of the dual-chamber system 3. A plug 23 that is embodied as a screw plug is preferred. It can thus act as a plunger element, wherein a plunger rod (not shown) can be engaged with the internal thread of the screw plug 23 with the aid of an external thread. Thus compressive forces can be introduced in a very simple manner into the second chamber 5' and thus indirectly into the separating element 7 which lead to an activation of the dual-chamber systems 3.

After the closure of the second chamber 5', the container 11 can be closed again and discharged from the clean room. It is also possible to omit the closing of the container 11 and optionally to discharge the container 11 open from the clean room or to remove only the magazine 9 or even the individual dual-chamber systems 3 from the clean room. Since namely both chambers 5, 5' of the dual chamber systems 3 are tightly closed, it is not necessary to continue to leave the dual chamber systems 3 in a sterile and/or aseptic environment.

This shows that the production method according to the invention and the pre-sterilizable carrier system according to the invention are advantageous compared to known methods and devices for filling dual-chamber systems. According to the invention it is possible for a manufacturing pharmaceutical company to use a standardized form of packaging directly on standardized filling lines. Products that are determined for freeze drying can hereby be filled on installations that are designed for pre-sterilizable systems. In known methods heavy and expensive metal magazines are used for filling dual-chamber systems in connection with materials that are to be fed to a freeze drying, which magazines are reused and therefore have to be autoclaved in a complex manner. In the present case a standardized form of packaging is used during the entire filling process instead of magazines of this type, which form of packaging is preferably fed to a single use and is thereafter disposed of. Since the carrier system according to the invention is gas-permeable but can be sealed in an impermeable manner for germs, viruses or bacteria, it is possible to arrange the filling and the freeze drying remotely from one another, which further makes it possible to carry out the freeze drying in an unsterile environment. The contents of the carrier system thereby remain sterile at all times. The carrier system can interact in a particularly simple manner with closures 19 known per se which are embodied as Lyo closures, if at least the container 11 comprises an elastically deformable plastic or preferably is composed thereof. It is hereby possible to combine the advantages of the carrier system with the advantages of the closures 19 known per se. In particular, due to the elastic deformability of the container 11, they can be pushed very easily and in a manner known per se from a first click-stop position into a second click-stop position in which they tightly close a chamber 5 of the dual-chamber systems 3. If the container 11 is sealed with a gas-permeable closure element 13 before the freeze drying, only hygienically closed containers are handled in the semi-automatic, automatic or manual loading and unloading of the freeze dryer so that here too a clearly lower contamination risk exists than is the case with known methods.

The invention claimed is:

1. A method for filling dual-chamber systems in pre-sterilizable carrier systems, the method comprising:
providing at least one dual-chamber system each having first and second chambers separated by a separating element, the at least one dual-chamber system accommodated by a magazine, the magazine and the at least one dual-chamber system disposed in a container, the container closed by a container closure element;
feeding the container into a clean room;
opening the container and filling the first chamber of the at least one dual-chamber system with a solution;
closing the first chamber of the at least one dual-chamber system with a gas-permeable closure element;
freeze drying the solution contained in the first chamber of the at least one dual-chamber system;
filling the second chamber of the at least one dual-chamber system;
closing the second chamber of the at least one dual-chamber system; and
discharging the container from the clean room.

2. A method for filling dual-chamber systems in pre-sterilizable carrier systems, the method comprising:
providing at least one dual-chamber system each including first and second chambers separated by a separating element, the at least one dual-chamber system accommodated by a magazine, the magazine and the at least one dual-chamber system disposed in a container, the container closed by a container closure element;
feeding the container into a clean room;
opening the container and filling the first chamber of the at least one dual-chamber system with a solution;
closing the first chamber of the at least one dual-chamber system with a gas-permeable closure element;
closing the container with the container closure element;
freeze drying the solution contained in the first chamber of the at least one dual-chamber system;
opening the container and filling the second chamber of the at least one dual-chamber system; and
closing the second chamber of the at least one dual-chamber system; and
discharging the container from the clean room.

3. The method according to claim 2, wherein the magazine is at least partially constructed of plastic.

4. The method according to claim 2, wherein the container is at least partially constructed of plastic.

5. The method according to claim 4, wherein the plastic is elastically deformable.

6. The method according to claim 5 further, comprising:
placing the container into a device for freeze drying arranged outside the clean room, in which device the freeze drying takes place, and after the freeze drying removing the container from the device and feeding the container into a clean room again.

7. The method according to claim 6, wherein the device for freeze drying itself is not sterile and/or aseptic.

8. The method according to claim 2, further comprising turning over the magazine after the closure of the first chamber and before the filling of the second chamber of the at least one dual-chamber system.

9. The method according to claim 2, further comprising closing the first chamber of the at least one dual-chamber system with a tamper-proof closure.

10. The method according to claim 2, further comprising closing the second chamber of the at least one dual-chamber system with a plug.

11. The method according to claim 10, further comprising closing the second chamber of the at least one dual-chamber system with a screw plug.

12. A method of filling a dual-chamber system in a pre-sterilizable carrier system, the dual chamber system having first and second chambers separated by a separating element, the dual-chamber system accommodated in a magazine, the magazine sealed in a container, the method comprising:
feeding the container into a clean room;
opening the container and filling the first chamber with a solution;
closing the first chamber;
freeze-drying the solution contained in the first chamber;
filling the second chamber;
closing the second chamber; and
discharging the container from the clean room.

* * * * *